United States Patent [19]

Kohn

[11] 4,358,591

[45] Nov. 9, 1982

[54] 1-PHENYL-3-POLYHALOALKYL(VINYL)-SULFENYL URACILS

[75] Inventor: Gustave K. Kohn, Palo Alto, Calif.

[73] Assignee: Zoecon Corporation, Palo Alto, Calif.

[21] Appl. No.: 170,480

[22] Filed: Jul. 21, 1980

[51] Int. Cl.³ .................. C07D 239/55; C07D 239/54
[52] U.S. Cl. ..................................... 544/311; 544/314
[58] Field of Search ............................... 544/311, 314

[56] References Cited

U.S. PATENT DOCUMENTS 4,266,056  5/1981  Henrick et al. ..................... 544/314

Primary Examiner—Paul M. Coughlan, Jr.
Attorney, Agent, or Firm—Donald W. Erickson; Jacqueline S. Larson; Thomas T. Gordon

[57] ABSTRACT

Novel 1-phenyl-3-polyhaloalkyl or polyhalovinyl uracils, and synthesis thereof, which are useful biological agents.

9 Claims, No Drawings

1-PHENYL-3-POLYHALOALKYL(VINYL)SULFENYL URACILS

This invention relates to novel 1-phenyl-3-polyhaloalkyl or polyhalovinyl uracils and the synthesis thereof, which are useful biological agents.

The 1-phenyl-3-polyhaloalkyl or polyhalovinyl uracils of the present invention are represented by the following formula A:

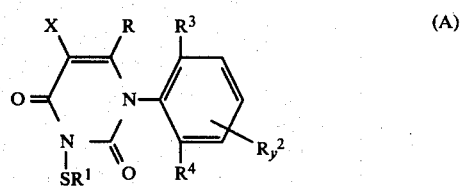

wherein,
R is hydrogen, methyl or ethyl;
$R^1$ is polyhaloalkyl or polyhalovinyl;
$R^2$ is lower alkyl, lower alkoxy, bromo, chloro, fluoro, lower haloalkyl, cyano, nitro, lower alkylthio, hydroxy, lower alkylcarbonyl, lower alkoxycarbonyl, lower haloalkoxy, cycloalkyl, or cycloalkalkyl;
$R^3$ is hydrogen or independently selected from the values of $R^2$;
$R^4$ is hydrogen or independently selected from the values of $R^2$;
X is hydrogen, carbamoyl, or cyano; and
Y is zero, one, two or three.

The compounds of formula A can be synthesized by the reaction of a 1-phenyl uracil with a polyhaloalkylsulfenyl halide or a polyhalovinylsulfenyl halide in the presence of an alkali metal. The synthesis is generally conducted by reacting an alkali metal salt of the 1-phenyl uracil in a reaction medium which may be water, an organic solvent such as an aromatic hydrocarbon, an alcohol or a halogenated hydrocarbon, or a mixture thereof with the desired sulfenyl halide. The sulfenyl halide may be diluted in an organic solvent inert to the reaction, such as a hydrocarbon or a halogenated hydrocarbon solvent, prior to addition to the reaction medium. The reaction is generally conducted at about room temperature or lower and with agitation of the reaction medium.

The term "polyhaloalkyl", as used herein, refers to polyhalomethyl and polyhaloethyl wherein the halo group is bromo, chloro or fluoro. The term "polyhaloalkyl" includes trichloromethyl; dichlorofluoromethyl; bromodichloromethyl; trifluoromethyl; tribromomethyl; 1,1,2,2-tetrachloroethyl; pentachloroethyl; 1,2-dibromo-1,2-dichloroethyl; 1,2,2-trichloroethyl; 1,1,2-trichloroethyl; 1,2,2,2-tetrachloroethyl; 2-chloro-1,2,2-tribromoethyl; 2-bromo-1,1,2-trichloroethyl; 2-bromo-1,2,2-trichloroethyl; 2-chloro-1,2-dibromoethyl; and 2-fluoro-1,1,2,2-tetrachloroethyl. The term "polyhalovinyl", as used herein, refers to polyhalovinyl wherein the halo group is bromo, chloro, or fluoro. The term "polyhalovinyl" includes trichlorovinyl; 2-bromo-1,2-dichlorovinyl; and 2-fluoro-1,2-dichlorovinyl.

The term "lower alkyl", as used herein, refers to a lower alkyl group of one to six carbon atoms. The term "lower alkoxy", as used herein, refers to a lower alkoxy group of one to six carbon atoms. The term "lower alkylthio", as used herein, refers to a lower alkylthio group of one to six carbon atoms. The term "lower haloalkyl", as used herein, refers to a lower alkyl group substituted with one to three atoms of bromine, chlorine or fluorine. The term "lower haloalkoxy", as used herein, refers to a lower alkoxy group substituted with one to three atoms of bromine, chlorine or fluorine. The term "lower alkylcarbonyl", as used herein, refers to a lower alkylcarbonyl group of two to seven carbon atoms. The term "cycloalkyl", as used herein, refers to a cycloalkyl group of three to six carbon atoms. The term "cycloalkalkyl", as used herein, refers to a cycloalkalkyl group of four to seven carbon atoms.

The compounds of the present invention are useful biological agents for the control of, for example, fungal and bacterial diseases. The compounds of the present invention are solids which can be applied topically using solid or liquid formulations containing from about 0.01 to 10.0 percent, by weight, or higher of a compound of the present invention. Many of the compounds of the present invention have systemic activity which is particularly advantageous for the control of fungal diseases of plants caused by microorganisms such as members of the Piricularia, Xanthomonas and Erwinia groups. The compounds of the present invention are part of a class of compounds known as sulfenimides, which have excellent utility as fungicides. See, for example, U.S. Pat. Nos. 2,553,770, 3,178,447 and 4,087,540; and J. R. Plimmer, Pesticide Chemistry in the 20th Century, ACS Symposium Series 37, "The Sulfenimide Fungicides," by G. K. Kohn, pp. 153–169 (1977) and references cited therein. Formulations and methods of application utilized in the application of prior art sulfenimides are applicable to the compounds of the present invention.

The 1-phenyl uracil starting materials of the following formula:

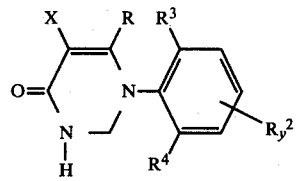

wherein R, $R^2$, $R^3$, $R^4$, X and y are as defined above, can be prepared following the methods of Senda et al., Chem. Pharm. Bull. 20(7), 1380–1388 (1972) and 22(1), 189–195 (1974) and the examples provided hereinafter.

The following examples are provided to illustrate the practice of the present invention. Temperature is given in degrees Centigrade.

EXAMPLE 1

A mixture of N-ethoxycarbonylcyanoacetamide (42 g), triethylorthoformate (40 g) and acetic anhydride (100 ml) is heated at reflux for one hour. The reaction is allowed to stand until cool and then is filtered, washing with ether, to yield α-cyano-β-ethoxy-N-ethoxycarbonylacrylamide.

To α-cyano-β-ethoxy-N-ethoxycarbonylacrylamide (1.2 g), dissolved in about 5 ml of boiling ethanol, is added 0.6 g of 2,6-dimethylaniline. The reaction is refluxed for several hours and then hexane is added. On cooling, the reaction is filtered, and washed with ethanol and ether to give α-cyano-β-(2,6-dimethylanilino)-N-ethoxycarbonylacrylamide, m.p. 138°–140°.

A mixture of α-cyano-β-(2,6-dimethylanilino)-N-ethoxycarbonylacrylamide (1.2 g) and about 10 ml of p-cymene is heated at reflux for about 1.5 hour. After cooling on standing, the crystalline product is collected by filtering and washing with ether to yield 5-cyano-1-(2,6-dimethylphenyl)uracil, m.p. 267°–269°.

To an ice cold solution of 2.40 g of sodium hydroxide in 70 ml of water is added 14.46 g (0.06 mol) of 5-cyano-1-(2,6-dimethylphenyl)uracil. Then 100 ml of dichloromethane is added. To this mixture, at 5°, is added 6.6 ml (0.06 mol) of trichloromethane sulfenyl chloride in two volumes of dichloromethane. The mixture is stirred approximately 22 min at 5°. Then the phases are separated and the organic phase is washed with ice cold water. The dichloromethane solution is dried over magnesium sulfate, filtered and stripped. The residue is triturated with ether/pentane, filtered and dried to obtain the crude product, which is then purified by crystallization to yield 5-cyano-1-(2,6-dimethylphenyl)-3-trichloromethanesulfenyluracil, m.p. 223°–225.5°.

EXAMPLE 2

A mixture of α-cyano-β-ethoxy-N-ethoxycarbonylacrylamide (10 g) and 45 ml of ethanol is heated to affect dissolution. Then 8.12 g of p-trifluoromethylaniline in 10 ml of ethanol is added and the mixture heated at reflux for 45 minutes. The mixture is cooled and filtered to give 14.01 g of α-cyano-β-(4-trifluoromethylanilino)-N-ethoxycarbonylacrylamide, which is added to about 60 ml of tetralin and heated at reflux for several hours. On formation of precipitate, the mixture is allowed to cool and then filtered, washed with ether, to yield 5-cyano-1-(4-trifluoromethylphenyl)uracil, m.p. 230.5°–231.5°.

To 290 mg of NaOH in 15 ml of water, cooled in an ice bath, is added 1.0 g (3.56 mol) of 5-cyano-1-(4-trifluoromethylphenyl)uracil. Then 15 ml of dichloromethane is added, followed by 0.725 ml of trichloromethanesulfenyl chloride in 1.5 ml of dichloromethane. The mixture is stirred for approximately 2 hr at 5°. Then dichloromethane and ice cold water are added and the layers separated. The organic phase is washed with ice cold water, dried over MgSO4 and evaporated. The product is taken up with ether, filtered and washed again with ether to yield 5-cyano-3-trichloromethanesulfenyl-1-(4-trifluoromethylphenyl)uracil, m.p. 167°–168.5°.

EXAMPLE 3

Following the method of Example 2, 4-fluoroaniline (0.05 mol) is reacted with α-cyano-β-ethoxy-N-ethoxycarbonylacrylamide (0.05 mol) and heated at reflux in tetralin to yield 5-cyano-1-(4-fluorophenyl)uracil, which is then reacted with trichloromethanesulfenyl chloride, in NaOH and dichloromethane, to yield the final product, 5-cyano-1-(4-fluorophenyl)-3-trichloromethanesulfenyluracil, m.p. 163°–165.5°.

In like manner, 5-cyano-1-(2,4-difluorophenyl)uracil is prepared, starting with 2,4-difluoroaniline, and is then reacted with trichloromethanesulfenyl chloride, giving 5-cyano-1-(2,4-difluorophenyl)-3-trichloromethanesulfenyluracil, m.p. 196°–198°.

EXAMPLE 4

Following the procedures hereinabove, each of 4-chloroaniline, 2,6-difluoroaniline, 4-methoxyaniline, 3-fluoroaniline, 2,6-dichloroaniline, 2,4,6-trichloroaniline, 3,4-dichloroaniline, 3,5-dichloroaniline, 2-methoxyaniline, 4-nitroaniline, 4-ethylaniline, 4-methoxy-2-methylaniline, 4-(N,N-dimethyl)aniline, 2-bromoaniline, 4-methylaniline, 4-isopropylaniline, 4-t-butylaniline, 4-acetylaniline, 2-fluoroaniline, 2-cyanoaniline, 4-methylthioaniline, 2-fluoro-4-methylaniline, 4-chloro-2-fluoroaniline, 4-fluoro-2-methylaniline, 4-trifluoromethylthioaniline, 2-chloro-4-cyanoaniline, 4-chloro-2,6-difluoroaniline, 4-chloro-2-cyanoaniline, 2,4-dimethoxyaniline, 2-chloro-6-methylaniline, 4-cyclopropylaniline, 2,6-dimethyl-4-t-butylaniline, 2,4,6-trimethylaniline, 4-chloro-2,6-dimethylaniline, 2-trifluoromethylaniline, 3,4-methylenedioxyaniline, 4-bromo-2-fluoroaniline, 2-fluoro-4-trifluoromethylaniline, 2-chloro-4-trifluoromethylaniline, and 2-methyl-4-trifluoromethylaniline is reacted with α-cyano-β-ethoxy-N-ethoxycarbonylacrylamide to yield the respective β-anilino compound. Each β-anilino compound is cyclized to yield the respective 5-cyano-1-substituted phenyl uracil under col. I, which is then reacted with trichloromethanesulfenyl chloride to yield the final product under col. II.

I 5-cyano-1-(4-chlorophenyl)uracil
5-cyano-1-(2,6-difluorophenyl)uracil
5-cyano-1-(4-methoxyphenyl)uracil
5-cyano-1-(3-fluorophenyl)uracil
5-cyano-1-(2,6-dichlorophenyl)uracil
5-cyano-1-(2,4,6-trichlorophenyl)uracil
5-cyano-1-(3,4-dichlorophenyl)uracil
5-cyano-1-(3,5-dichlorophenyl)uracil
5-cyano-1-(2-methoxyphenyl)uracil
5-cyano-1-(4-nitrophenyl)uracil
5-cyano-1-(4-ethylphenyl)uracil
5-cyano-1-(4-methoxy-2-methylphenyl)uracil
5-cyano-1-(4-(N,N-dimethyl)phenyl)uracil
5-cyano-1-(2-bromophenyl)uracil
5-cyano-1-(4-methylphenyl)uracil
5-cyano-1-(4-isopropylphenyl)uracil
5-cyano-1-(4-t-butylphenyl)uracil
5-cyano-1-(4-acetylphenyl)uracil
5-cyano-1-(2-fluorophenyl)uracil
5-cyano-1-(2-cyanophenyl)uracil
5-cyano-1-(4-methylthiophenyl)uracil
5-cyano-1-(2-fluoro-4-methylphenyl)uracil
5-cyano-1-(4-chloro-2-fluorophenyl)uracil
5-cyano-1-(4-fluoro-2-methylphenyl)uracil
5-cyano-1-(4-trifluoromethylthiophenyl)uracil
5-cyano-1-(2-chloro-4-cyanophenyl)uracil
5-cyano-1-(4-chloro-2,6-difluorophenyl)uracil
5-cyano-1-(4-chloro-2-cyanophenyl)uracil
5-cyano-1-(2,4-dimethoxyphenyl)uracil
5-cyano-1-(2-chloro-6-methylphenyl)uracil
5-cyano-1-(4-cyclopropylphenyl)uracil
5-cyano-1-(2,6-dimethyl-4-t-butylphenyl)uracil
5-cyano-1-(2,4,6-trimethylphenyl)uracil
5-cyano-1-(4-chloro-2,6-dimethylphenyl)uracil
5-cyano-1-(2-trifluoromethylphenyl)uracil
5-cyano-1-(3,4-methylenedioxyphenyl)uracil
5-cyano-1-(4-bromo-2-fluorophenyl)uracil
5-cyano-1-(2-fluoro-4-trifluoromethylphenyl)uracil
5-cyano-1-(2-chloro-4-trifluoromethylphenyl)uracil
5-cyano-1-(2-methyl-4-trifluoromethylphenyl)uracil

II 5-cyano-1-(4-chlorophenyl)-3-trichloromethanesulfenyluracil
5-cyano-1-(2,6-difluorophenyl)-3-trichloromethanesulfenyluracil
5-cyano-1-(4-methoxyphenyl)-3-trichloromethanesulfenyluracil
5-cyano-1-(3-fluorophenyl)-3-trichloromethanesulfenyluracil
5-cyano-1-(2,6-dichlorophenyl)-3-trichloromethanesulfenyluracil, m.p. 131.5°–133°
5-cyano-1-(2,4,6-trichlorophenyl)-3-trichloromethanesulfenyluracil, m.p. 230°–231°
5-cyano-1-(3,4-dichlorophenyl)-3-trichloromethanesulfenyluracil
5-cyano-1-(3,5-dichlorophenyl)-3-trichloromethanesulfenyluracil
5-cyano-1-(2-methoxyphenyl)-3-trichloromethanesulfenyluracil
5-cyano-1-(4-nitrophenyl)-3-trichloromethanesulfenyluracil
5-cyano-1-(4-ethylphenyl)-3-trichloromethanesulfenyluracil
5-cyano-1-(4-methoxy-2-methyl)-3-trichloromethanesulfenyluracil
5-cyano-1-[4-(N,N-dimethyl)phenyl]-3-trichloromethanesulfenyluracil
5-cyano-1-(2-bromophenyl)-3-trichloromethanesulfenyluracil
5-cyano-1-(4-methylphenyl)-3-trichloromethanesulfenyluracil
5-cyano-1-(4-isopropylphenyl)-3-trichloromethanesulfenyluracil
5-cyano-1-(4-t-butylphenyl)-3-trichloromethanesulfenyluracil
5-cyano-1-(4-acetylphenyl)-3-trichloromethanesulfenyluracil
5-cyano-1-(2-fluorophenyl)-3-trichloromethanesulfenyluracil
5-cyano-1-(2-cyanophenyl)-3-trichloromethanesulfenyluracil
5-cyano-1-(4-methylthiophenyl)-3-trichloromethanesulfenyluracil
5-cyano-1-(2-fluoro-4-methylphenyl)-3-trichloromethanesulfenyluracil
5-cyano-1-(4-chloro-2-fluorophenyl)-3-trichloromethanesulfenyluracil
5-cyano-1-(4-fluoro-2-methylphenyl)-3-trichloromethanesulfenyluracil
5-cyano-3-trichloromethanesulfenyl-1-(4-trifluoromethylthiophenyl)uracil
5-cyano-1-(2-chloro-4-cyanophenyl)-3-trichloromethanesulfenyluracil
5-cyano-1-(4-chloro-2,6-difluorophenyl)-3-trichloromethanesulfenyluracil
5-cyano-1-(4-chloro-2-cyanophenyl)-3-trichloromethanesulfenyluracil
5-cyano-1-(2,4-dimethoxyphenyl)-3-trichloromethanesulfenyluracil
5-cyano-1-(2-chloro-6-methylphenyl)-3-trichloromethanesulfenyluracil
5-cyano-1-(4-cyclopropylphenyl)-3-trichloromethanesulfenyluracil
5-cyano-1-(2,6-dimethyl-4-t-butylphenyl)-3-trichloromethanesulfenyluracil
5-cyano-3-trichloromethanesulfenyl-1-(2,4,6-trimethylphenyl)uracil
5-cyano-1-(4-chloro-2,6-dimethylphenyl)-3-trichloromethanesulfenyluracil
5-cyano-3-trichloromethanesulfenyl-1-(2-trifluoromethylphenyl)uracil
5-cyano-1-(3,4-methylenedioxyphenyl)-3-trichloromethanesulfenyluracil
5-cyano-1-(4-bromo-2-fluorophenyl)-3-trichloromethanesulfenyluracil
5-cyano-1-(2-fluoro-4-trifluoromethylphenyl)-3-trichloromethanesulfenyluracil
5-cyano-1-(2-chloro-4-trifluoromethylphenyl)-3-trichloromethanesulfenyluracil
5-cyano-1-(2-methyl-4-trifluoromethylphenyl)-3-trichloromethanesulfenyluracil

EXAMPLE 5

To an ice cold solution of 1.60 g (0.04 mol) of NaOH in 45 ml of water is added 9.64 g (0.04 mol) of 5-cyano-1-(2,6-dimethylphenyl)uracil, obtained as in Example 1. After dissolution, 50 ml of ice cold dichloromethane is added, followed by a solution of 9.36 g (0.04 mol) of 1,1,2,2-tetrachloroethanesulfenyl chloride (prepared by the method of U.S. Pat. No. 3,395,180) in 15 ml of dichloromethane. The mixture is stirred for 30 min at 4°, after which time 50 mg of triethylbenzylammonium chloride is added and stirring is continued for another 30 min at 4°. The aqueous layer is separated and discarded. The dichloromethane solution is dried and stripped at aspirator pressure. The unreacted sulfenyl chloride is then removed by trituration with pentane/dichloromethane (4:1). The resultant crude product is purified by slurrying at 30° in 60 ml of ethanol-free chloroform, allowed to cool to RT and filtered. To the filtrate is added hexane to the cloud point, and the mixture is then filtered to yield 5-cyano-1-(2,6-dimethylphenyl)-3-(1,1,2,2-tetrachloroethanesulfenyl)uracil, m.p. 180°–183°.

The sodium salt of each of 5-cyano-1-(2-methylphenyl)uracil, 5-cyano-1-(2-chlorophenyl)uracil, 5-cyano-1-(2,6-dichlorophenyl)uracil, 5-cyano-1-(2,6-dimethylphenyl)-6-methyluracil, 5-carbamoyl-1-(2,6-dimethylphenyl)uracil and 1-(2,6-dimethylphenyl)uracil is reacted with 1,1,2,2-tetrachloroethanesulfenyl chloride to yield the respective below-listed compound:
5-cyano-1-(2-methylphenyl)-3-(1,1,2,2-tetrachloroethanesulfenyl)uracil
5-cyano-1-(2-chlorophenyl)-3-(1,1,2,2-tetrachloroethanesulfenyl)uracil
5-cyano-1-(2,6-dichlorophenyl)-3-(1,1,2,2-tetrachloroethanesulfenyl)uracil
5-cyano-1-(2,6-dimethylphenyl)-6-methyl-3-(1,1,2,2-tetrachloroethanesulfenyl)uracil
5-carbamoyl-1-(2,6-dimethylphenyl)-3-(1,1,2,2-tetrachloroethanesulfenyl)uracil
1-(2,6-dimethylphenyl)-3-(1,1,2,2-tetrachloroethanesulfenyl)uracil

EXAMPLE 6

Following the procedure of Example 1, the sodium salt of each of 5-cyano-1-(2,6-dimethylphenyl)-6-methyluracil, 5-carbamoyl-1-(2,6-dimethylphenyl)uracil and 1-(2,6-dimethylphenyl)uracil is reacted with trichloromethanesulfenyl chloride to yield 5-cyano-1-(2,6-dimethylphenyl)-6-methyl-3-trichloromethanesulfenyluracil, 5-carbamoyl-1-(2,6-dimethylphenyl)-3-trichloromethanesulfenyluracil and 1-(2,6-dimethylphenyl)-3-trichloromethanesulfenyluracil.

EXAMPLE 7

Following the procedure of Example 5, the sodium salt of 5-cyano-1-(2,6-dimethylphenyl)uracil and 5-cyano-1-(2-methylphenyl)uracil is each reacted with 2-fluoro-1,1,2,2-tetrachloroethanesulfenyl chloride to yield 5-cyano-1-(2,6-dimethylphenyl)-3-(2-fluoro-1,1,2,2-tetrachloroethanesulfenyl)uracil and 5-cyano-1-(2-methylphenyl)-3-(2-fluoro-1,1,2,2-tetrachloroethanesulfenyl)uracil.

Following the procedure of Example 1, trichloromethanesulfenyl chloride is reacted with the sodium salt of each of 5-cyano-1-(2-ethylphenyl)uracil, 5-cyano-1-(2,6-diethylphenyl)uracil and 5-cyano-1-(2-isopropylphenyl)uracil to yield 5-cyano-1-(2-ethylphenyl)-3-trichloromethanesulfenyluracil, 5-cyano-1-(2,6-diethylphenyl)-3-trichloromethanesulfenyluracil and 5-cyano-1-(2-isopropylphenyl)-3-trichloromethanesulfenyluracil.

Similarly, bromodichloromethanesulfenyl chloride is reacted with the sodium salt of 5-cyano-1-(2-methylphenyl)uracil and 5-cyano-1-(2,6-dimethylphenyl)uracil to prepare 5-cyano-1-(2-methylphenyl)-3-bromodichloromethanesulfenyluracil and 5-cyano-1-(2,6-dimethylphenyl)-3-bromodichloromethanesulfenyluracil.

EXAMPLE 8

The sodium salt of 5-cyano-1-(2,6-dimethylphenyl)uracil is reacted with each of 1,2-dibromo-1,2-dichloroethanesulfenyl chloride and pentachloroethanesulfenyl chloride to yield 5-cyano-1-(2,6-dimethylphenyl)-3-(1,2-dibromo-1,2-dichloroethanesulfenyl)uracil and 5-cyano-1-(2,6-dimethylphenyl)-3-pentachloroethanesulfenyluracil.

Following the procedure of Example 5, trichloroethenesulfenyl chloride is reacted with the sodium salt of each of 5-cyano-1-(2,6-dimethylphenyl)uracil, 5-cyano-1-(2-methylphenyl)uracil, 5-cyano-1-(2-ethylphenyl)uracil and 5-cyano-1-(2,6-diethylphenyl)uracil to yield 5-cyano-1-(2,6-dimethylphenyl)-3-trichloroethenesulfenyluracil, 5-cyano-1-(2-methylphenyl)-3-trichloroethenesulfenyluracil, 5-cyano-1-(2-ethylphenyl)-3-trichloroethenesulfenyluracil and 5-cyano-1-(2,6-diethylphenyl)-3-trichloroethenesulfenyluracil.

EXAMPLE 9

The sodium salt of each of 5-cyano-1-(2,6-dimethylphenyl)uracil, 5-cyano-1-(2-methylphenyl)uracil, 5-cyano-1-(2-ethylphenyl)uracil and 5-cyano-1-(2,6-diethylphenyl)uracil is reacted with dichlorofluoromethanesulfenyl chloride using the procedure of Example 1 to yield 5-cyano-3-dichlorofluoromethanesulfenyl-1-(2,6-dimethylphenyl)uracil, m.p. 196.5°-198.5°, 5-cyano-3-dichlorofluoromethanesulfenyl-1-(2-methylphenyl)uracil, 5-cyano-3-dichlorofluoromethanesulfenyl-1-(2-ethylphenyl)uracil, and 5-cyano-3-dichlorofluoromethanesulfenyl-1-(2,6-diethylphenyl)uracil.

The sodium salt of 5-cyano-1-phenyluracil is reacted with each of dichlorofluoromethanesulfenyl chloride and trichloromethanesulfenyl chloride following the procedure of Example 1 to yield 5-cyano-3-dichlorofluoromethanesulfenyl-1-phenyluracil and 5-cyano-3-trichloromethanesulfenyl-1-phenyluracil, respectively.

EXAMPLE 10

Following the procedure of Example 2, the sodium salt of each of 5-cyano-1-(2-chloro-6-methylphenyl)uracil, 5-cyano-1-(2-methoxy-6-methylphenyl)uracil, and 5-cyano-1-(2-hydroxy-6-methylphenyl)uracil is reacted with trichloromethanesulfenyl chloride to yield 5-cyano-1-(2-chloro-6-methylphenyl)-3-trichloromethanesulfenyluracil, 5-cyano-1-(2-methoxy-6-methylphenyl)-3-trichloromethanesulfenyluracil and 5-cyano-1-(2-hydroxy-6-methylphenyl)-3-trichloromethanesulfenyluracil, respectively.

Rice seedlings at the one- to two-leaf stage were root drenched (10 ml) or sprayed with the chemical compound under test. Forty-eight hours later the plants were inoculated by cutting off the tips of the leaves with scissors dipped in a dispersion of a billion cells/ml ($10^9$ cells/ml) of *Xanthomonas oryzae.* After 7 days at 100% relative humidity at 30° C. the seedlings were assessed for disease on a 0–4 scale, where 0 is no control, 1 is slight control, 2 is fair control, 3 is good control and 4 is complete control. Results are shown in Table I below.

TABLE I

| Compound | Rate of Application in Parts per Million (p.p.m.) | Root Drench Test | Spray Test |
|---|---|---|---|
| Example No. 1 | 50 | 4 | 4 |
| | 10 | 3 | 3 |
| | 5 | 2 | 3 |
| Example No. 5 (first compound) | 50 | 4 | 3 |
| | 25 | 4 | 0 |

What is claimed is:

1. A compound of the following formula A:

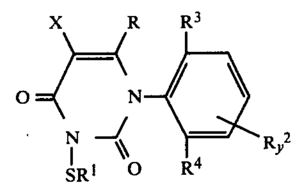

(A)

wherein,

R is hydrogen, methyl or ethyl;

$R^1$ is polyhalomethyl, polyhaloethyl or polyhalovinyl, wherein the halo group is bromo, chloro or fluoro;

$R^2$ is lower alkyl, lower alkoxy, bromo, chloro, fluoro, lower haloalkyl, cyano, nitro, lower alkylthio, hydroxy, lower alkylcarbonyl, lower alkoxycarbonyl, lower haloalkoxy, cycloalkyl, or cycloalkalkyl;

$R^3$ is hydrogen or independently selected from the values of $R^2$;

$R^4$ is hydrogen or independently selected from the values of $R^2$;

X is hydrogen, carbamoyl, or cyano; and y is zero, one, two or three.

2. A compound according to claim 1 wherein $R^1$ is polyhalomethyl.

3. A compound according to claim 2 wherein R is hydrogen, X is cyano, and y is zero or one.

4. A compound according to claim 1 wherein $R^1$ is trichloromethyl, R is hydrogen, X is cyano, y is zero or one, and each of $R^3$ and $R^4$ is hydrogen, lower alkyl of one to three carbon atoms, lower alkoxy of one to three carbon atoms, bromo, chloro, fluoro or lower haloalkyl of one to three carbon atoms.

5. A compound according to claim 4 wherein each of $R^3$ and $R^4$ is hydrogen, methyl or ethyl.

6. A compound according to claim 5 wherein y is zero.

7. A compound according to claim 5 wherein each of $R^3$ and $R^4$ is methyl and y is zero.

8. A compound according to claim 4 wherein at least one of $R^3$ and $R^4$ is hydrogen.

9. A compound according to claim 8 wherein each of $R^3$ and $R^4$ is hydrogen, $R^2$ is fluoro or trifluoromethyl and y is one.

* * * * *